United States Patent
Kotani et al.

(10) Patent No.: US 11,276,813 B2
(45) Date of Patent: Mar. 15, 2022

(54) COATING LIQUID COMPOSITION FOR ORIENTATIONAL PIEZOELECTRIC FILM, ORIENTATIONAL PIEZOELECTRIC FILM AND LIQUID EJECTION HEAD

(71) Applicant: CANON KABUSHIKI KAISHA, Tokyo (JP)

(72) Inventors: Yoshinori Kotani, Yokohama (JP); Yoshihiro Ohashi, Tokyo (JP); Motokazu Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 340 days.

(21) Appl. No.: 16/427,680

(22) Filed: May 31, 2019

(65) Prior Publication Data
US 2019/0393404 A1    Dec. 26, 2019

(30) Foreign Application Priority Data
Jun. 20, 2018    (JP) .............................. JP2018-116856

(51) Int. Cl.
*H01L 41/08*    (2006.01)
*C01G 25/00*    (2006.01)
(Continued)

(52) U.S. Cl.
CPC ........ *H01L 41/081* (2013.01); *B41J 2/14233* (2013.01); *C01G 25/006* (2013.01);
(Continued)

(58) Field of Classification Search
None
See application file for complete search history.

(56) References Cited

U.S. PATENT DOCUMENTS

2014/0048131 A1 *    2/2014    Tanaka ............ H01L 31/022425
                                                             136/256
2017/0155037 A1 *    6/2017    Kubota ............... H01L 41/0986

FOREIGN PATENT DOCUMENTS

JP    2015-107905 A    6/2015

OTHER PUBLICATIONS

Ohashi et al., U.S. Appl. No. 16/435,998, filed Jun. 10, 2019.
Ohashi et al., U.S. Appl. No. 16/440,098, filed Jun. 13, 2019.

* cited by examiner

*Primary Examiner* — Erica S Lin
(74) *Attorney, Agent, or Firm* — Venable LLP

(57) ABSTRACT

Use of a barium titanate based coating liquid composition comprising:
(a) a sol-gel source material containing
  (i) at least a barium component selected from a group consisting of barium alkoxides, hydrolyzates of barium alkoxides and condensates of hydrolyzates of barium alkoxides and (ii) at least a titanium component selected from a group consisting of titanium alkoxides, hydrolyzates of titanium alkoxides and condensates of hydrolyzates of titanium alkoxides; and
(b) a β-keto ester compound expressed by general formula (1) shown below:

(1)

(Continued)

where $R_1$ and $R_2$ independently represent respective alkyl groups having not less than 1 and not more than 6 carbon atoms.

12 Claims, 11 Drawing Sheets

(51) Int. Cl.
    *B41J 2/14*           (2006.01)
    *C09D 1/00*         (2006.01)
    *C07C 69/716*      (2006.01)

(52) U.S. Cl.
    CPC .............. *C07C 69/716* (2013.01); *C09D 1/00* (2013.01); *B41J 2002/14258* (2013.01); *C01P 2002/34* (2013.01); *C01P 2004/86* (2013.01)

COATING LIQUID COMPOSITION FOR ORIENTATIONAL PIEZOELECTRIC FILM, ORIENTATIONAL PIEZOELECTRIC FILM AND LIQUID EJECTION HEAD

BACKGROUND OF THE INVENTION

Field of the Invention

The present invention relates to a coating liquid composition for orientational piezoelectric film, to an orientational piezoelectric film and also to a liquid ejection head. More specifically, the present invention relates to a barium titanate based coating liquid composition, a method of manufacturing the same, a barium titanate based baked film and a liquid ejection head having such a film.

Description of the Related Art

In recent years, there has been an ever-increasing demand for lead-free dielectric thin films to be used in place of conventional lead titanate (PT) based dielectric thin films from the fear of environmental loads generated by disposed wastes of various electronic devices comprising lead-containing dielectric thin films. Attentions have been paid to the sol-gel method as method of manufacturing such lead-free thin films because the sol-gel method allows the complex compositions of such thin films to be accurately controlled and large area substrates to be uniformly coated with such a thin film. Barium titanate based thin films formed by the sol-gel method are known to date as lead-free dielectric thin films (see, inter alia, Japanese Patent Application Laid-Open No. 2015-107905).

While it has been known that dielectric thin films can suitably be used as actuators for inkjet recording heads and other applications, dielectric thin films to be used for such applications are required to show a large piezoelectric constant. Generally, highly orientational thin films tend show a large piezoelectric constant. Therefore, in addition to that coating liquid compositions to be used for forming such thin films are required to be compositionally stable from the manufacturing point of view as a matter of course, the thin films formed from such coating liquid compositions are also required to be highly oriented. Then, for the thin films formed from coating liquid compositions to be highly oriented, it is necessary to raise the degree of film crystallinity of the thin films.

However, coating films as described in the above-cited prior art literature are accompanied by a problem that they show only a low degree of film crystallinity and that they are not highly oriented unless they are formed on a single crystal base.

SUMMARY OF THE INVENTION

Therefore, an object of the present invention is to provide an orientational piezoelectric film that is highly oriented and also shows a high degree of crystallinity, a coating liquid composition for forming barium titanate based baked films to be more specific, and a method of manufacturing such a coating liquid composition.

Another object of the present invention is to provide an orientational piezoelectric film that is highly oriented and shows a high degree of crystallinity, a barium titanate based baked film to be more specific, by using such a coating liquid composition.

In a mode of carrying out the present invention, there is provided a barium titanate based coating liquid composition comprising:
(a) a sol-gel source material containing
(i) at least a barium component selected from a group consisting of barium alkoxides, hydrolyzates of barium alkoxides and condensates of hydrolyzates of barium alkoxides and
(ii) at least a titanium component selected from a group consisting of titanium alkoxides, hydrolyzates of titanium alkoxides and condensates of hydrolyzates of titanium alkoxides; and
(b) a β-keto ester compound expressed by general formula (1) shown below:

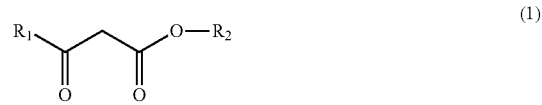

(1)

where $R_1$ and $R_2$ independently represent respective alkyl groups having not less than 1 and not more than 6 carbon atoms.

In another mode of carrying out the present invention, there is provided a barium titanate based baked film that is a crystal axis orientational piezoelectric film of a perovskite type crystal expressed by general formula (2) shown below:

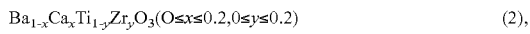

$$Ba_{1-x}Ca_xTi_{1-y}Zr_yO_3 (0 \leq x \leq 0.2, 0 \leq y \leq 0.2) \quad (2),$$

the orientational piezoelectric film being formed on a metal electrode having the (111) orientation, the orientational piezoelectric thin film being (111) oriented in pseudo-cubic notation.

Further features of the present invention will become apparent from the following description of exemplary embodiments with reference to the attached drawings.

DESCRIPTION OF THE EMBODIMENTS

Figure 1:
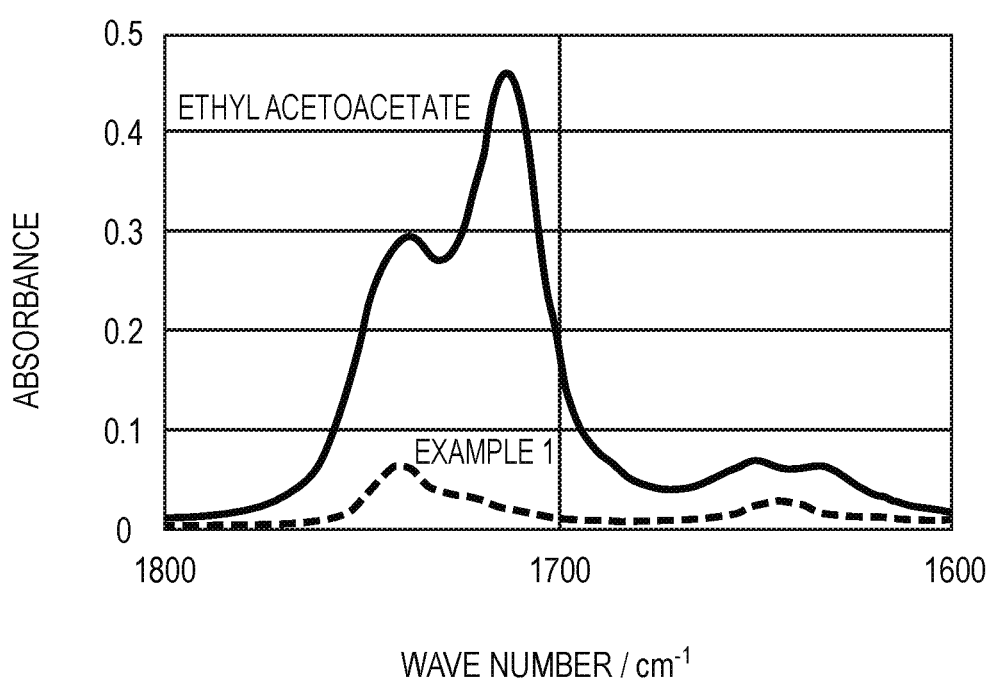
FIG. 1 is a schematic illustration of the results of observation of the infrared absorption spectrum of a coating liquid composition 1 obtained in Example 1.

Now, the present invention will be described in greater detail by referring to currently preferred embodiments of the present invention.

<Barium Titanate Based Coating Liquid Composition>

A barium titanate based coating liquid composition according to the present invention comprises as an indispensable component thereof (i) at least a barium component selected from a group consisting of barium alkoxides, hydrolyzates of barium alkoxides and condensates of hydrolyzates of barium alkoxides. Additionally, a barium titanate based coating liquid composition according to the present invention comprises as another indispensable component (ii) at least a titanium component selected from a group consisting of titanium alkoxides, hydrolyzates of titanium alkoxides and condensates of hydrolyzates of titanium alkoxides. Thus, a barium titanate based coating liquid composition according to the present invention comprises a sol-gel source material containing above-listed (i) and (ii).

Furthermore, a barium titanate based coating liquid composition according to the present invention comprises a β-keto ester compound expressed by general formula (1) shown below:

(1)

where $R_1$ and $R_2$ independently represent respective alkyl groups having not less than 1 and not more than 6 carbon atoms.

Compounds that can be used for the source compound of the metal oxide in a barium titanate based coating liquid composition according to the present invention include alkoxides of various metals, hydrolyzates thereof, condensates of hydrolyzates thereof and chlorides and salts such as nitrates of various metals. However, the use of any of metal alkoxides as source material is preferable from the viewpoint of stability of the coating liquid composition obtained by using the source material and film uniformity at the time of film formation using the coating liquid composition.

Additionally, a barium titanate based coating liquid composition according to the present invention may contain as optional component (iii) at least a calcium component selected from a group consisting of calcium alkoxides, hydrolyzates of calcium alkoxides and condensates of hydrolyzates of calcium alkoxides.

Furthermore, a barium titanate based coating liquid composition according to the present invention may contain also as optional component (iv) at least a zirconium component selected from a group consisting of zirconium alkoxides, hydrolyzates of zirconium alkoxides and condensates of hydrolyzates of zirconium alkoxides.

Examples of barium alkoxides that can be used for the purpose of the present invention include dimethoxy barium, diethoxy barium, di-i-propoxy barium, di-n-propoxy barium, di-i-butoxy barium, di-n-butoxy barium and di-sec-butoxy barium. Examples of titanium alkoxides that can be used for the purpose of the present invention include tetramethoxy titanium, tetraethoxy titanium, tetra-n-propoxy titanium, tetraisopropoxy titanium, tetra-n-butoxy titanium and tetraisobutoxy titanium. Examples of calcium alkoxides that can be used for the purpose of the present invention include dimethoxy calcium, diethoxy calcium, di-n-propoxy calcium and di-n-butoxy calcium. Examples of zirconium alkoxides that can be used for the purpose of the present invention include zirconium tetraethoxide, zirconium tetra n-propoxide, zirconium tetraisopropoxide, zirconium tetra n-butoxide and zirconium tetra t-butoxide.

When any of the above-listed metal alkoxides is employed for the purpose of the present invention, it will very quickly be hydrolyzed by the moisture in the air or the water that is added thereto to produce a clouded solution and/or precipitation because it is highly reactive to water. In order to prevent such hydrolysis from taking place and stabilize the solution of the metal alkoxide, preferably a stabilizing agent is added to the solution.

For the purpose of the present invention, a β-keto ester compound expressed by general formula (1) shown above is employed as stabilizing agent.

Beside the β-keto ester compound expressed by the general formula (1), one or more compounds selected from a group consisting of other β-keto ester compounds, β-diketones, amines and glycols may additionally be employed so long as the use of any of compounds does not impair the advantages of the present invention. The expression of "a β-keto ester compound" as used hereinafter refers to a β-keto ester compound expressed by general formula (1).

Not only the solution is stabilized but also the obtained baked film shows a high degree of crystallinity by using a β-keto ester compound expressed by general formula (1).

More specific examples of β-keto ester compounds that are expressed by the above general formula (1) include methyl acetoacetate, ethyl acetoacetate, butyl acetoacetate, isobutyl acetoacetate, sec-butyl acetoacetate, tert-butyl acetoacetate, hexyl acetoacetate, ethyl 3-oxohexanoate and methyl isobutyl acetate.

Preferably, the stabilizing agent is added by 1.5 to 4.5 times of the total moles of the metal alkoxide. More preferably, the stabilizing agent is added so as to make the number of moles thereof to be 2 to 4 times of the total moles of the metal alkoxide. The stability of the coating liquid composition can be improved by adding the stabilizing agent in the above-described manner.

Note that the β-keto ester compound, which is the above-described stabilizing agent, and the metal element of the metal alkoxide presumably are interacting with each other in the coating liquid composition according to the present invention. For the purpose of the present invention, the expression of a barium alkoxide precursor, a titanium alkoxide precursor, a calcium alkoxide precursor or a zirconium alkoxide precursor refers to the substance that is produced by an intermolecular interaction of the metal alkoxide and the β-keto ester compound.

A barium titanate based coating liquid composition according to the present invention can be prepared by dissolving and refluxing the stabilizing agent and the metal alkoxide as described above in an organic solvent. Preferably the organic solvent is added so as to make the member of moles thereof to be 20 to 30 times of the total moles of the metal alkoxide.

Specific examples of organic solvents that can be used for the purpose of the present invention include alcohols, carboxylic acids, aliphatic hydrocarbons, alicyclic hydrocarbons, aromatic hydrocarbons, esters, ketones, ethers and mixtures of two or more of any of the above-listed organic solvents.

Specific examples of alcohols that can preferably be used for the purpose of the present invention include methanol, ethanol, 2-propanol, butanol, 2-methoxy ethanol, 2-ethoxy ethanol, 1-methoxy-2-propanol, 1-ethoxy-2-propanol, 1-propoxy-2-propanol, 4-methyl-2-pentanol, 2-ethyl butanol, 3-methoxy-3-methyl butanol, ethylene glycol, diethylene glycol and glycerin.

Specific examples of carboxylic acids that can preferably be used for the purpose of the present invention include n-butyric acid, α-methyl butyrate, i-valeric acid, 2-ethyl butyrate, 2,2-dimethyl butyrate, 3,3-dimethyl butyrate, 2,3-dimethyl butyrate, 3-methylpentanoic acid, 4-methylpentanoic acid, 2-ethylpentanoic acid, 3-ethylpentanoic acid, 2,2-dimethylpentanoic acid, 3,3-dimethylpentanoic acid, 2,3-dimethylpentanoic acid, 2-ethylhexanoic acid and 3-ethylhexanoic acid.

Specific examples of aliphatic hydrocarbons and alicyclic hydrocarbons that can preferably be used for the purpose of the present invention include n-hexane, n-octane, cyclohexane, cyclopentane and cyclooctane.

Specific examples of aromatic hydrocarbons that can preferably be used for the purpose of the present invention include toluene, xylene and ethylbenzene. Specific examples of esters that can preferably be used for the purpose of the present invention include ethyl formate, ethyl acetate, n-butyl acetate, ethylene glycol monomethyl ether acetate, ethylene glycol monoethyl ether acetate and ethylene glycol monobutyl ether acetate.

Specific examples of ketones that can preferably be used for the purpose of the present invention include acetone, methyl ethyl ketone, methyl isobutyl ketone and cyclohexanone.

Specific examples of ethers that can preferably be used for the purpose of the present invention include dimethoxy ethane, tetrahydrofuran, dioxane and diisopropyl ether.

When manufacturing a barium titanate based coating liquid composition according to the present invention, any of the above-listed alcohols is preferably selected from the above-cited various solvents from the viewpoint of stability of the solution.

A method of manufacturing a barium titanate based coating liquid composition according to the present invention comprises steps (1) through (3) as listed below. More specifically, the method comprises (1) a step of adding a β-keto ester compound to a selected organic solvent, (2) a step of adding a sol-gel source material containing (i) a barium component described previously and (ii) a titanium component described previously to the organic solvent and (3) a step of refluxing the organic solvent.

Additionally, the above step (2) of the manufacturing method includes a step of further adding a sol-gel source material containing (iii) a calcium component described previously.

Still additionally, the above step (2) of the manufacturing method further includes a step of adding a sol-gel source material containing (iv) a zirconium component described previously.

For example, after mixing the metal alkoxide with the solution prepared by adding the stabilizing agent to the organic solvent, the mixture solution is preferably heated to a temperature range between 80 and 200° C. for 2 to 10 hours in other words, the mixture solution is preferably refluxed under the above-described conditions.

Whenever necessary, the alkoxyl group is preferably partially hydrolyzed in advance by adding water and a catalyzer. Specific examples of catalyzers that can be used for the partial hydrolysis include nitric acid, hydrochloric acid, sulfuric acid, phosphoric acid, acetic acid and ammonia. In other words, a barium titanate based coating liquid composition according to the present invention may additionally comprise the hydrolysate and the condensate thereof of the metal alkoxide.

Whenever necessary, a water-soluble organic polymer may be added to a barium titanate based coating liquid composition according to the present invention. Specific examples of water-soluble organic polymers that can be used as additive include polyethylene glycol, polypropylene glycol and polyvinyl pyrrolidone. The selected water-soluble organic polymer may preferably be added by 0.1 to 10 masses relative to the total mass of the oxide of the film.

<Barium Titanate Based Baked Film>

A barium titanate based baked film according to the present invention is a baked film of a barium titanate based coating liquid composition as described above that has the structure of perovskite type crystal expressed by general formula (2) shown below:

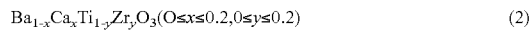

$$Ba_{1-x}Ca_xTi_{1-y}Zr_yO_3 (0 \leq x \leq 0.2, 0 \leq y \leq 0.2) \quad (2)$$

and is (111) oriented in pseudocubic notation.

Note here that a barium titanate (BT) based film has the rhombohedral structure, the orthorhombic structure, the tetragonal structure or the cubic structure or a plurality of the above-listed ones. Therefore, unless specifically noted otherwise, it will be treated as pseudocubic hereinafter is this letter of specification for the sake of simplicity of notation.

For the purpose of the present invention, the composition ratio of calcium and zirconium in the above formula (2) is within the respective ranges of $0 \leq x \leq 0.2$ and $0 \leq y \leq 0.2$. Preferably, the ratio is within the range of $0 \leq x \leq 0.1$ and $0 \leq y \leq 0.1$. Additionally, the ratio of (Ba+Ca) to (Ti+Zr) may be shifted from 1 so long as the ratio is found within the range of $0.95 \leq (Ba+Ca)/(Ti+Zr) \leq 1.05$. Preferably, the ratio is within the range of $1.00 \leq (Ba+Ca)/(Ti+Zr) \leq 1.02$.

When forming a coating film by using a barium titanate based coating liquid composition according to the present invention, it is preferable to create a dry atmosphere (a dry air atmosphere or a dry inert gas atmosphere such as a dry nitrogen atmosphere) for the atmosphere in which the coating operation is conducted. Preferably, the relative humidity of the dry atmosphere is not more than 30%.

Besides, examples of techniques that can be used for applying a coating liquid composition according to the present invention in order to form a coating film include dipping, spin coating, spraying, printing, flow coating and a combination of two or more of the above-listed techniques. In other words, any known application technique can appropriately be adopted for the purpose of the present invention. The film thickness can be controlled by changing the pulling speed, when the dipping method is adopted, or by changing the rotation speed of the substrate, when the spin coating method is adopted, and by changing the concentration of the coating solution.

The substrate on which a barium titanate based baked film according to the present invention is to be formed is not subject to any particular limitations so long as the formed barium titanate based baked film is (111) oriented in pseudocubinc notation. Examples of preferable substrates that can be used for the purpose of the present invention include heat-resistant substrates such as silicon substrates in which a metal electrode that is oriented along the (111) plane (to be also referred to as lower electrode hereinafter) is formed and sapphire substrates. A metal material such as Pt or Ir that is electroconductive and does not react with a barium titanate based baked film according to the present invention is employed for the lower electrode to be formed on the substrate. Alternatively, a substrate on which a lower electrode has been formed with an adhesion layer and an insulator film interposed between them may be employed. Specific examples of substrates that can be used for the purpose of the present invention include substrates having a multilayer structure (lower electrode/adhesion layer/insulator film/substrate) such as Pt/Ti/SiO$_2$/Si, Pt/TiO$_2$/SiO$_2$/Si, Pt/Ir/SiO$_2$/Si and Pt/IrO/Ir/SiO$_2$/Si.

After forming a coating film on the substrate, the coating film is calcinated and then baked for crystallization. The calcination is to be executed under predetermined conditions by using a hot plate or an infrared condenser (RTA). The calcination is preferably executed in the air, in an oxygen atmosphere or in a steam-containing atmosphere because the objective of the calcination is to remove the solvent and, at the same time, to thermolyze or hydrolyze the metal compound to turn it into a complex oxide. If the calcination is executed and the coating film is heated in the air, the moisture necessary for the hydrolysis is satisfactorily secured by the moisture content of the air. Note that, prior to the calcination, the coating film may be subjected to a low temperature heating process at 60 to 200° C. for 1 to 20 minutes by means of a hot plate or the like in order to remove in particular the low boiling point components and the adsorbed moisture. The calcination is preferably executed at a temperature between 400 and 600° C. for 1 to 20 minutes. If the desired film thickness is secured by means of a single application step, the steps from the application of the coating liquid composition to the calcination may be executed only once and then the applied and calicinated film is subjected to a baking process. Alternatively, the steps from the application of the coating liquid composition to the calcination may be repeated for a plurality of times until the desired film thickness is obtained before the applied and calicinated film is finally subjected to a baking process. The film thickness that is obtained by a single application of the coating liquid composition is somewhere between 50 and 500 nm and the obtained film thickness is preferably small when the calcination temperature is low. The baking process is a step of baking the applied and calcinated film at temperatures not lower the crystallization temperature in order to crystallize the film. Then, a barium titanate based baked film according to the present invention is obtained as a result of the baking process. Oxygen, nitrogen, argon or a mixture gas of two or more of them may preferably be employed for the baking atmosphere of the crystallization step. The baking process is preferably executed while the baking temperature is held to 800 to 1,100° C. for 1 to 60 minutes. The rapid thermal annealing (RTA) technique may be used for the baking process. The rate at which the temperature is raised from the room temperature to the baking temperature is preferably 10 to 100° C./sec.

A barium titanate based baked film according to the present invention is obtained by using a barium titanate based coating liquid composition according to the present invention and by way of the above-described steps. The obtained barium titanate based baked film comprises a perovskite type crystal expressed by general formula (2) and is (111) oriented. Preferably, a barium titanate based baked film according to the present invention has a Pt electrode or an Ir electrode as substrate base. A (111) oriented film can be obtained by making a barium titanate based baked film by epitaxially orientating the film along the (111) plane of the metal electrode.

While the mechanism of (111) orientation may not necessarily be based on the theory that will be described below, the inventors of the present invention believe that the theory may highly probably be verifiable. More specifically, the inventors of the present invention believes that the timing of releasing the stabilizing agent from the metal alkoxide and that of generation of crystal nuclei affect the orientation of the film. When the coordination ability of the stabilizing agent contained in a barium titanate based coating liquid composition of the present invention is low, the stabilizing agent can easily be released and the crystal grain growth can easily progress in the crystal grain growth stage that arises as a result of the film baking process so that the barium titanate based baked film becomes epitaxially oriented along (111) plane of the substrate base such as the Pt electrode or the Ir electrode and a (111) oriented film can be obtained. Then, as a result, it is expectable to improve the piezoelectric characteristics of the film. The coordination ability of the stabilizing agent as mentioned above refers to the interaction between the metal element of the metal alkoxide and the stabilizing agent.

As for the coordination ability of the stabilizing agent, the coordination state (the interaction of the metal element of the metal alkoxide and the stabilizing agent) exerts influence on the metal element of the metal alkoxide. For example, it is generally so considered that, when a β-keto ester compound is employed for the stabilizing agent, the oxygen atom of the carbonyl group of the β-keto ester compound is coordinated (interacts) with the metal element. The coordination state can be evaluated by means of IR spectrum observation and, by observing the peak profiles in the region from 1,800 cm$^{-1}$ to 1,600 cm$^{-1}$ that are attributable to the carbonyl group, it will be found that the peak profiles of the β-keto ester compound itself that is not in a coordinated state differs from the peak profiles of the β-keto ester compound that is in a coordinated state.

More specifically, when ethyl acetoacetate is employed and the intensity of the peak at or near 1,745 cm$^{-1}$ and the intensity of the peak at or near 1,720 cm$^{-1}$ that are attributable to the carbonyl group in the keto form are compared, it will be found that the intensity of the peak at 1,745 cm$^{-1}$ is lower than the intensity of the peak at 1,720 cm$^{-1}$ for the ethyl acetoacetate source material itself. On the other hand, in the instance of ethyl acetoacetate contained in a coating liquid composition according to the present invention, it will be found that the intensity of the peak at 1,745 cm$^{-1}$ is higher than the intensity of the peak at 1,720 cm$^{-1}$. Additionally, as for the peak profiles at or near 1,645 cm$^{-1}$ and at or near 1,630 cm$^{-1}$ that are attributable to the carbonyl group in the enol form differ between the ethyl acetoacetate source material and the ethyl acetoacetate contained in a coating liquid composition according to the present invention.

In a coating liquid, ethyl acetoacetate inevitably is influenced by other source materials located around ethyl acetoacetate molecules, metal alkoxide in particular. In other words, it cannot exist in a state of being totally free from the influence of those other source materials. Therefore, it may be safe to presume that the change in the peak profiles is caused by the interaction between the carbonyl group of ethyl acetoacetate and the metal element of metal alkoxide to a considerable extent. Thus, the inventors of the present invention believe that the use of a coating liquid in which a metal alkoxide precursor has been formed allows crystal grain growth to easily progress in the film baking process and the epitaxial orientation along the (111) plane of the substrate having a Pt electrode or an Ir electrode is promoted to make it possible to obtain a highly (111) oriented film.

<Liquid Ejection Head>

A liquid ejection head according to the present invention comprises a liquid ejection orifice, a pressure chamber held in communication with the a liquid ejection orifice and an actuator for causing a capacity change of the pressure chamber to take place in order to eject liquid from the liquid ejection orifice. The actuator has a vibrating plate, a lower electrode, a piezoelectric film, which is a barium titanate based baked film formed on a substrate, and an upper electrode that are arranged in the above mentioned order as viewed from the pressure chamber side.

Figure 8:
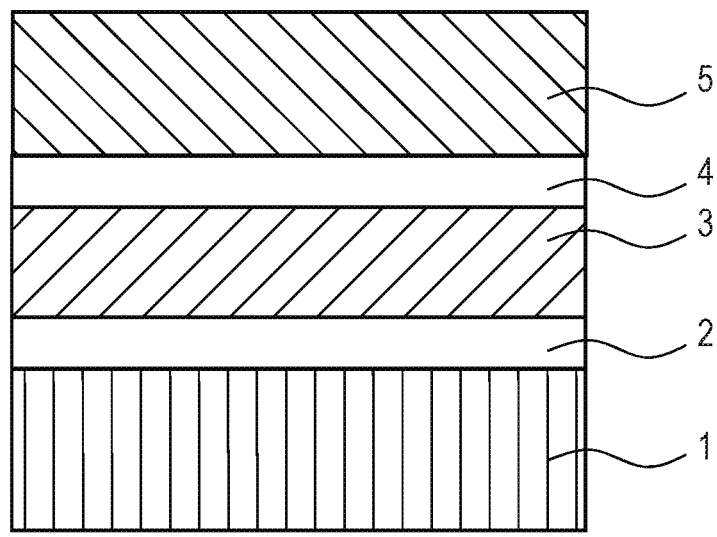
FIG. 8 is a schematic vertical crosssectional view of a piezoelectric actuator that can be used for the purpose of the present invention.

FIG. 8 is a schematic vertical crosssectional view of an actuator that can be used for the purpose of the present invention. In FIG. 8, 1 denotes a lower substrate, 2 denotes an intermediate layer and 3 denotes a lower electrode, while 4 denotes an orientation control layer and 5 denotes a piezoelectric film.

The material of the lower substrate 1 is preferably one that contains $SiO_2$ at least in the uppermost surface layer thereof. Additionally, the material is preferably neither deformed nor molten when subjected to thermal load during the drying step that comes after the coating liquid composition applying process. Preferably, the lower substrate 1 has a smooth surface and can prevent atoms from being diffused in any heat treatment in addition to that it shows satisfactory mechanical strength. Furthermore, when manufacturing a liquid ejection head for this embodiment by using a piezoelectric film, which is a barium titanate based baked film, the lower substrate 1 may be made to operate also as the vibrating pate of the pressure chamber to be used for forming the pressure chamber. For instance, while a silicon (Si)-made semiconductor substrate having an $SiO_2$ surface layer, which is formed by thermal oxidation, may preferably be employed for the purpose of manufacturing a liquid ejection head, a ceramic substrate of zirconia, alumina or silica may alternatively be employed. If the substrate has an $SiO_2$ uppermost surface layer, any of the above-listed plurality of materials may be employed in combination to form a substrate having a multilayer structure.

The intermediate layer 2 is a layer having a role of causing the lower $SiO_2$ layer and the upper electrode to tightly adhere to each other. Without an intermediate layer, Pt, which is the metal of the upper electrode, and $SiO_2$, which is an oxide, do not tightly adhere to each other and additionally the electrode and the piezoelectric layer, which will be formed thereon, will only poorly be crystallized so that no satisfactory piezoelectric performance will be achieved. Furthermore, the intermediate layer should not be too thick. If the thickness of the intermediate layer exceeds 30 nm, the crystallinity of the upper piezoelectric layer will accordingly be degraded. Therefore, the thickness of the intermediate layer is preferably not less than 5 nm and less than 50 nm. Ti or a Ti oxide, which may typically be $TiO_2$, is preferably employed as the material of the intermediate layer 2.

The lower electrode 3 is a 5 to 2,000 nm thick electro-conductive layer and examples of materials that can be used for the lower electrode 3 of a piezoelectric element include metals such as Ti, Pt, Ta, Ir, Sr, In, Sn, Au, Al, Fe, Cr and Ni and oxides of such metals. While there are several techniques that can be used to form the lower electrode 3, including the sol-gel method, the sputtering method and the vapor deposition method, the use of the sputtering method is most preferable because an electrode can be formed without raising the temperature of the material by means of the sputtering method. While the thickness of the electrode is not subject to any particular limitations so long as the electro-conductivity of the electrode is secured, it is desirably between 10 and 1,000 nm. The formed electrode may be subjected to a patterning process in order to make it show a desired profile. The electrode material is preferably a metal that is (111) oriented in pseudocubic notation as pointed out earlier.

The orientation control layer 4 has the role of controlling the orientation of the piezoelectric film laid thereon. The technique to be used for forming the orientation control layer 4 is not subject to any particular limitations.

A baked film obtained by applying, calcinating and baking a barium titanate based coating liquid composition according to the present invention is employed for the piezoelectric film 5.

Figure 9:
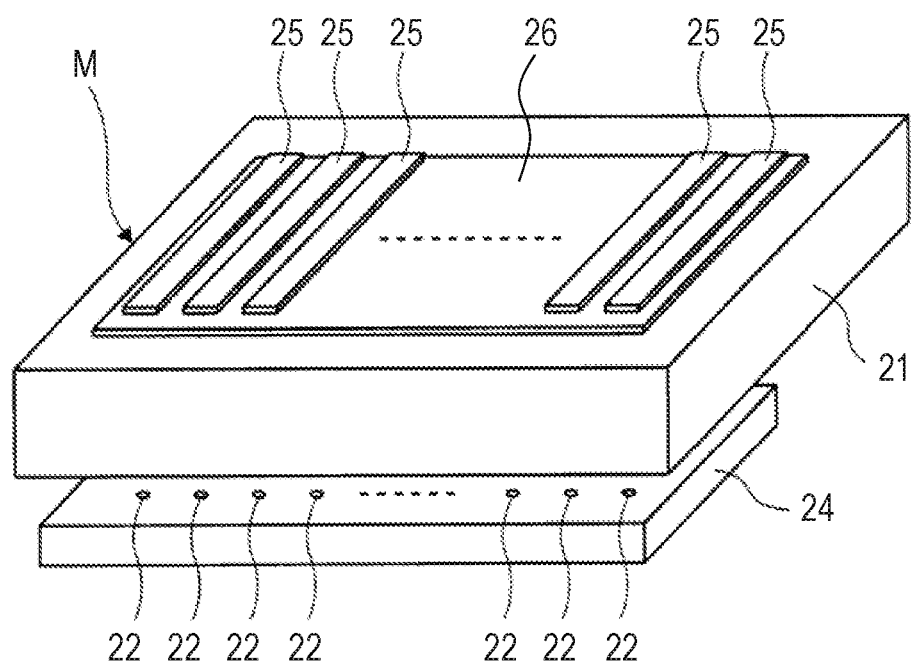
FIG. 9 is a schematic perspective view of an embodiment of liquid ejection head according to the present invention.
Figure 10:
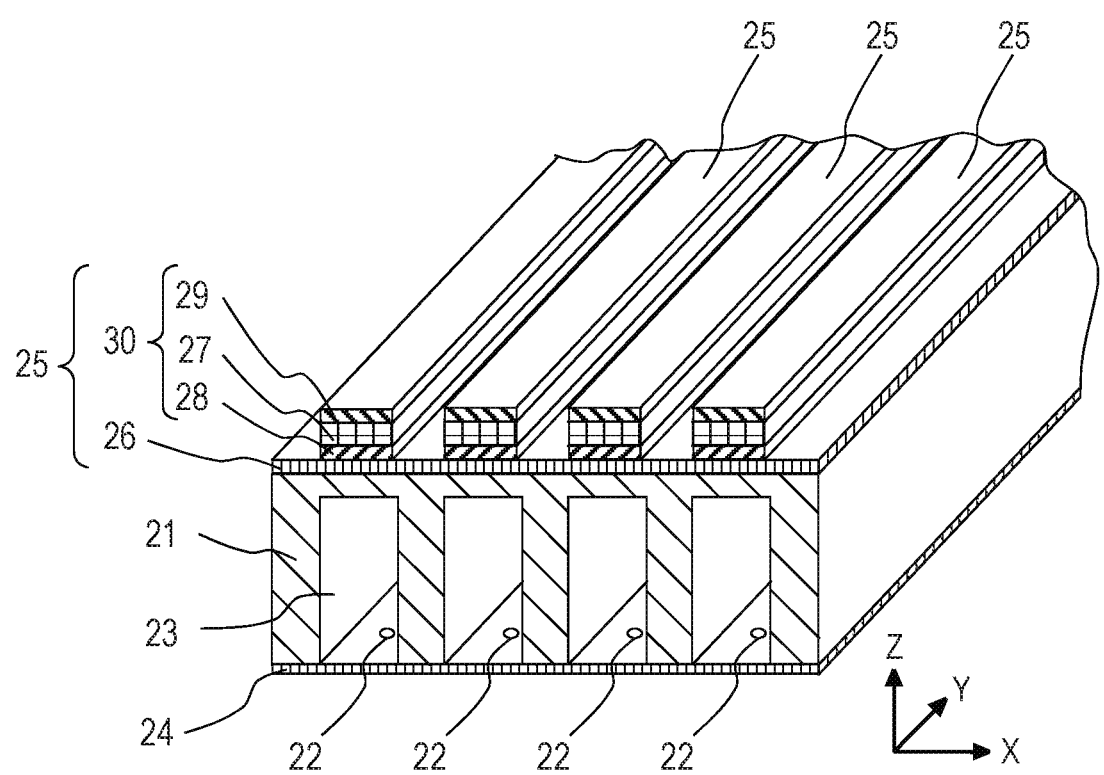
FIG. 10 is a schematic perspective crosssectional view of the embodiment of liquid ejection head according to the present invention shown in FIG. 9.
Figure 11:
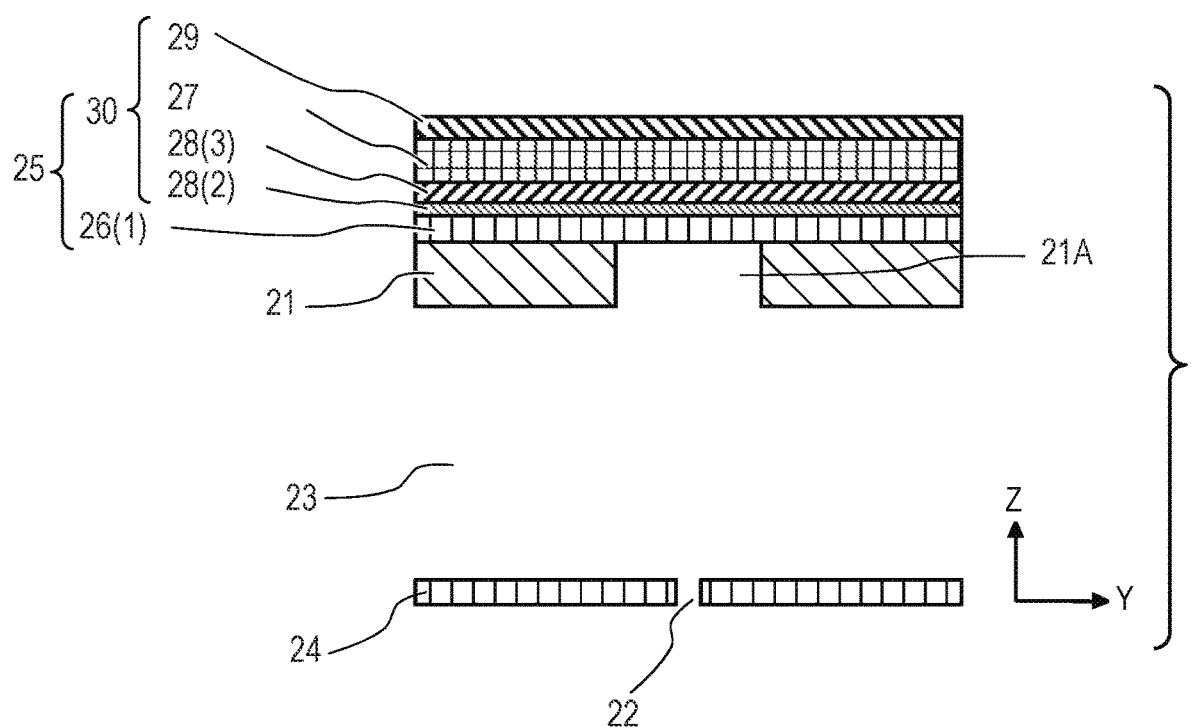
FIG. 11 is a schematic crosssectional view of the embodiment of liquid ejection head according to the present invention shown in FIG. 9.

An embodiment of liquid ejection head according to the present invention comprises a piezoelectric film and has a configuration as shown in FIGS. 9 through 11. More specifically, this liquid ejection head M comprises a substrate 21 to be used for a liquid ejection head, a plurality of liquid ejection orifices 22, a plurality of pressure chambers 23 and actuators 25 arranged respectively in the corresponding pressure chambers 23. The pressure chambers 23 are arranged to correspond to the respective liquid ejection orifices 22 and respectively held in communication with the corresponding liquid ejection orifices 22. As each of the actuators 25 vibrates, the capacity of the corresponding one of the pressure chambers 23 is changed so as to eject liquid from the corresponding liquid ejection orifice 22. The liquid ejection orifices 22 are formed at predetermined regular intervals in a nozzle plate 24, while the pressure chambers 23 are formed in the substrate 21 of the liquid ejection head in array so as to positionally correspond to the respective liquid ejection orifices 22. Note that the liquid ejection orifices 22 are respectively arranged so as to face the lower sides of the corresponding actuators 25, they may alternatively be arranged at the lateral sides of the respective corresponding actuators 25. The substrate 21 of the liquid ejection head is provided on the upper surface thereof with openings (not shown) to correspond to the respective pressure chambers 23 and the actuators 25 are respectively so arranged as to close the corresponding openings. The actuators 25 are formed by using a vibrating plate 26 and respective piezoelectric elements 30 and each of the piezoelectric elements 30 comprises a piezoelectric film 27 and a pair of electrodes (a lower electrode 28 and an upper electrode 29). While the material of the vibrating plate 26 is not subject to any particular limitations, a semiconductor material, a metal, a metal oxide or glass may preferably be used to form the vibrating plate 26. The piezoelectric elements 30 may securely be fitted to the vibrating plate 26 by means of bonding or adhesion or, alternatively, the lower electrodes 28 and the piezoelectric thin films 30 may directly be formed on the vibrating plate 26, using the vibrating plate 26 as substrate. Still alternatively, the vibrating plate 26 may directly be formed on a substrate 21 to be used for forming the liquid ejection head.

Liquid to be used for the purpose of the present invention may typically be ink. Thus, a liquid ejection head according to the present invention may typically be an inkjet recording head.

EXAMPLES

Now, the present invention will be described in greater detail by way of examples and comparative examples.

Note, however, the examples that are described hereinafter do not limit the scope of the present invention by any means.

An infrared absorption spectrometer ("Spectrum One": trade name, available from Perkinelmer Japan, using an ATR attachment) was employed to observe the infrared absorption spectrum in the examples.

A scanning electron microscope (SEM, "Quanta FEG 250": trade name, available from FFI) and an electron backscatter diffraction analyzer ("TSL-EBSD System": trade name, available from TSL Solutions) were employed for the purpose of film cross section observations, color mapping of orientation and inverse pole figure orientation mapping in each of the examples and the comparative examples.

(Example 1) Preparation of Coating Liquid Composition 1

Coating liquid composition 1 was prepared by dissolving barium di-i-propoxide, titanium n-butoxide and zirconium n-butoxide into a solution formed by adding ethyl acetoacetate as stabilizing agent to a mixed solvent of 2-methoxyethanol and 3-methoxybutanol and subsequently refluxing the solution for about 8 hours. An 85% zirconium n-butoxide–1-butanol solution was used as the source material of the zirconium n-butoxide. As for the molar ratio of the components of the solution, the ratio of 2-methoxyethanol: 3-methoxybutanol:ethyl acetoacetate:barium di-i-propoxide:titanium n-butoxide:zirconium n-butoxide was made to be equal to 18:12:3:1.0:0.97:0.03.

FIG. 1 shows the results of the observation of the infrared absorption spectrum of the coating liquid composition 1 prepared in this example. For the purpose of comparison, the spectrum obtained for the source material of ethyl acetoacetate was also shown in FIG. 1. The peak at 1,745 cm$^{-1}$ and the peak at 1.720 cm$^{-1}$ are attributable to the keto form, whereas the peak at 1,645 cm$^{-1}$ and the peak at 1,630 cm$^{-1}$ are attributable to the enol form. By comparing the intensity of the peak at 1,745 cm$^{-1}$ and the intensity of the peak at 1,720 cm$^{-1}$ that are attributable to the carbonyl group in the keto form, it is found that the intensity of the peak at 1,745 cm$^{-1}$ is lower than the intensity of the peak at 1,720 cm$^{-1}$ for the ethyl acetoacetate of the source material, whereas the intensity of the peak at 1,745 cm$^{-1}$ is lower than the intensity of the peak at 1,720 cm$^{-1}$ for the ethyl acetoacetate contained in the coating liquid composition 1. With regard to the peaks attributable to the carbonyl group in the enol form, it is also found that the intensities of the peaks for ethyl acetoacetate of the source material differ from the intensities of the peaks for the ethyl acetoacetate contained in the coating liquid composition.

(Examples 2 and 3, Comparative Examples 1 Through 4) Preparation of Coating Liquid Compositions 2 Through 7

Coating liquid compositions 2 through 7 were prepared as in Example 1 by using the stabilizing agents expressed by general formula (3) as shown below and listed in Table 1.

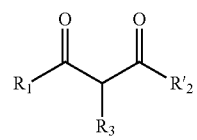

(3)

TABLE 1

| | stabilizing agent | $R_1$ | $R'_2$ | $R_3$ | coating liquid composition |
|---|---|---|---|---|---|
| Example 1 | ethyl acetoacetate | —CH$_3$ | —OC$_2$H$_5$ | —H | 1 |
| Example 2 | butyl acetoacetate | —CH$_3$ | —OC$_4$H$_9$ | —H | 2 |
| Example 3 | ethyl 3-oxohexanoate | —C$_3$H$_7$ | —OC$_2$H$_5$ | —H | 3 |
| Com. Ex. 1 | ethyl 2-methylacetoacetate | —CH$_3$ | —OC$_2$H$_5$ | —CH$_3$ | 4 |
| Com. Ex. 2 | ethyl 2-ethylacetoacetate | —CH$_3$ | —OC$_2$H$_5$ | —C$_2$H$_5$ | 5 |
| Com. Ex. 3 | acetyl acetone | —CH$_3$ | —CH$_3$ | —H | 6 |
| Com. Ex. 4 | 3-methyl-2,4-pentanedione | —CH$_3$ | —CH$_3$ | —CH$_3$ | 7 |

(Example 4) Preparation of Barium Titanate Baked Film 1

Figure 2:
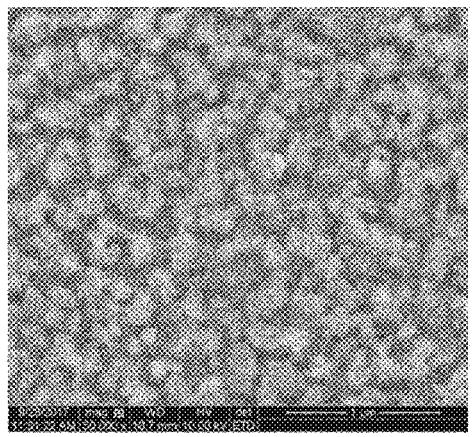
FIG. 2 is an electron micrograph of the surface of a barium titanate based baked film 1 obtained in Example 4.

A coating film was formed on an SiO$_2$/Si substrate by means of the spin coating method, using the coating liquid composition 1 prepared in Example 1. The substrate carrying the coating film was heat-treated on a hot plate at 130° C. for 2 minutes and then additionally heat-treated at 450° C. for 5 minutes. Subsequently, the substrate carrying the coating film was heat-treated in an infrared heating furnace at 1,000° C. for 10 minutes. The film thickness of the obtained barium titanate baked film was about 50 nm. FIG. 2 shows a surface SEM photograph of the barium titanate baked film 1. It will be seen that the crystal grain growth has considerably progressed and the obtained baked film is a highly crystalline film.

(Example 5) Preparation of Barium Titanate Baked Film 2

Figure 3:
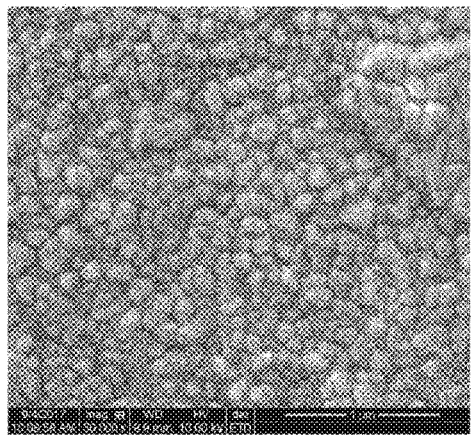
FIG. 3 is an electron micrograph of the surface of a barium titanate based baked film 2 obtained in Example 5.

A coating film was formed by using the coating liquid composition 1 prepared in Example 1 on a (111)Pt/SiO$_2$/Si substrate that had in advance been subjected to an annealing process at 1,000° C. by means of the spin coating method. For the purpose of calcination, the applied composition was heat-treated at 130° C. for 2 minutes on a hot plate and subsequently further heat-treated at 450° C. for 5 minutes. The application and calcination was repeated for 10 times and finally the applied and calcinated composition was baked in an infrared heating furnace at 1,000° C. for 10 minutes. The film thickness of the obtained barium titanate baked film 2 was about 1 µm. FIG. 3 shows an SEM photograph of the surface of the barium titanate baked film 2. It will be seen from FIG. 3 that there was a remarkable progress of crystal grain growth and hence the baked film was a highly crystalline film. A color map of orientation of the obtained film was observed by means of electron backscatter diffraction analysis. The blue part that indicates a (111) plane occupied almost all the area of the obtained color map. From the above, it was found that the barium titanate baked film 2 obtained in this example had almost completely been (111) oriented.

(Example 6) Preparation of Barium Titanate Baked Film 3

Figure 4:
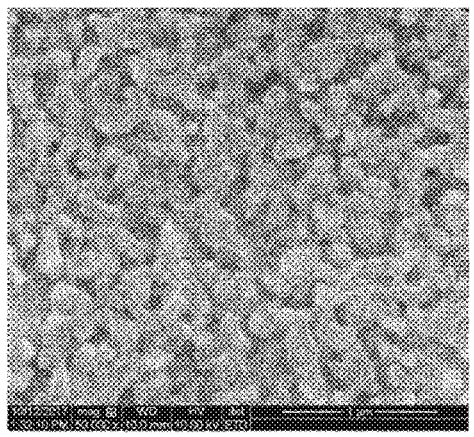
FIG. 4 is an electron micrograph of the surface of a barium titanate based baked film 3 obtained in Example 6.

Barium titanate baked film 3 of this example was prepared by using the coating liquid composition 2 prepared in Example 2 and following procedures similar to those of Example 4. FIG. 4 shows an SEM photograph of the surface of the obtained barium titanate baked film 3. Like the barium titanate baked film 1 obtained in Example 4, there was a remarkable progress of crystal grain growth in this example and hence the baked film was a highly crystalline film. It was found by observing a color map of orientation of the barium titanate baked film prepared by following procedures similar to those of Example 5 that the baked film had been (111) oriented.

(Example 7) Preparation of Barium Titanate Baked Film 4

Figure 5:
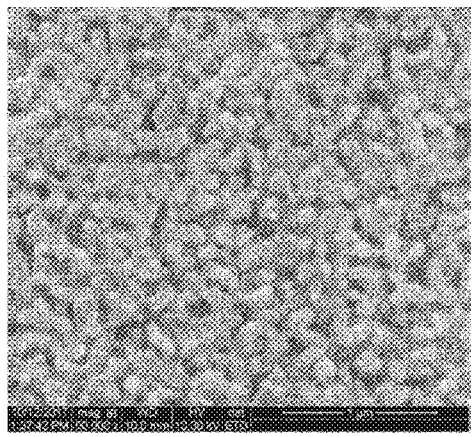
FIG. 5 is an electron micrograph of the surface of a barium titanate based baked film 4 obtained in Example 7.

Barium titanate baked film 4 of this example was prepared by using the coating liquid composition 3 prepared in Example 3 and following procedures similar to those of Example 4. FIG. 5 shows an SEM photograph of the surface of the obtained barium titanate baked film 4. Like the barium titanate baked film 1 obtained in Example 4, there was a remarkable progress of crystal grain growth in this example and hence the baked film was a highly crystalline film. It was found by observing a color map of orientation of the barium titanate baked film prepared by following procedures similar to those of Example 5 that the baked film had been (111) oriented.

(Comparative Example 5) Preparation of Barium Titanate Baked Film 5

Figure 6:
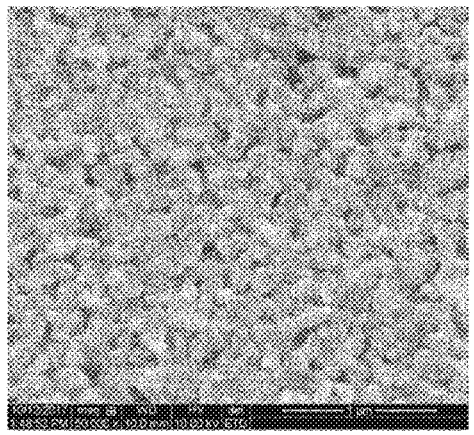
FIG. 6 is an electron micrograph of the surface of a barium titanate based baked film 5 obtained in Comparative Example 5.

Barium titanate baked film 5 of this comparative example was prepared by using the coating liquid composition 4 prepared in Comparative Example 1 and following procedures similar to those of Example 4. FIG. 6 shows an SEM photograph of the surface of the obtained barium titanate baked film 5. Unlike the barium titanate baked film 1 obtained in Example 4, there was no remarkable progress of crystal grain growth and hence the baked film was a poorly crystalline film.

(Comparative Example 6) Preparation of Barium Titanate Baked Film 6

Figure 7:
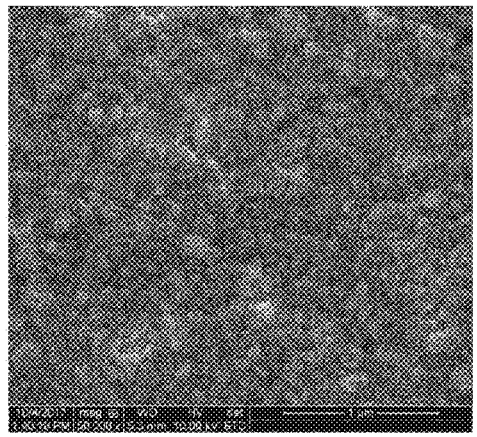
FIG. 7 is an electron micrograph of the surface of a barium titanate based baked film 6 obtained in Comparative Example 6.

Barium titanate baked film 6 of this comparative example was prepared by using the coating liquid composition 4 and following procedures similar to those of Example 5. FIG. 7 shows an SEM photograph of the surface of the obtained barium titanate baked film 6. Like the barium titanate baked film 5, there was no remarkable progress of crystal grain growth and hence the baked film was a poorly crystalline film. It was found by observing a color map of orientation of the barium titanate baked film obtained by electron backscatter diffraction analysis that there were several colors sparsely existing in a scattered manner. From the above, it was found that the barium titanate baked film 6 obtained by using the coating liquid composition 4 was randomly oriented.

(Comparative Example 7) Preparation of Barium Titanate Baked Film 7

Barium titanate baked film 7 of this comparative example was prepared by using the coating liquid composition 5 prepared in Comparative Example 2 and following procedures similar to those of Example 4. Unlike the barium titanate baked film 1 obtained in Example 4, it was found as a result of observing an SEM photograph of the surface of the obtained barium titanate baked film 7 that there was no remarkable progress of crystal grain growth and hence the baked film was a poorly crystalline film. Additionally, it was found as a result of observing a color map of orientation of the barium titanate baked film obtained by electron backscatter diffraction analysis that the barium titanate baked film prepared by following procedures similar to those of Example 5 was randomly oriented.

(Comparative Example 8) Preparation of Barium Titanate Baked Film 8

Barium titanate baked film 8 of this comparative example was prepared by using the coating liquid composition 6 prepared in Comparative Example 3 and following procedures similar to those of Example 4. Unlike the barium titanate baked film 1 obtained in Example 4, it was found as a result of observing an SEM photograph of the surface of the obtained barium titanate baked film 8 that there was no remarkable progress of crystal grain growth and hence the baked film was a poorly crystalline film. Additionally, it was found as a result of observing a color map of orientation of the barium titanate baked film obtained by electron backscatter diffraction analysis that the barium titanate baked film prepared by following procedures similar to those of Example 5 was randomly oriented.

(Comparative Example 9) Preparation of Barium Titanate Baked Film 9

Barium titanate baked film 9 of this comparative example was prepared by using the coating liquid composition 7 prepared in Comparative Example 4 and following procedures similar to those of Example 4. Unlike the barium titanate baked film 1 obtained in Example 4, it was found as a result of observing an SEM photograph of the surface of the obtained barium titanate baked film 9 that there was no remarkable progress of crystal grain growth and hence the baked film was a poorly crystalline film. Additionally, it was found as a result of observing a color map of orientation of the barium titanate baked film that the barium titanate baked film prepared by following procedures similar to those of Example 5 was randomly oriented.

Thus, the present invention can provide a highly oriented barium titnate based film. Additionally, the present invention can provide a stable coating liquid composition for forming such a film and also a method of manufacturing such a film.

Therefore, the present invention can provide a highly oriented piezoelectric film, more specifically a barium titanate based baked film.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-116856, filed Jun. 20, 2018, which is hereby incorporated by reference herein in its entirety.

What is claimed is:

1. A barium titanate based coating liquid composition comprising:
   (a) a sol-gel source material containing:
      (i) at least a barium component selected from the group consisting of barium alkoxides, hydrolyzates of barium alkoxides, and condensates of hydrolyzates of barium alkoxides; and
      (ii) at least a titanium component selected from the group consisting of titanium alkoxides, hydrolyzates of titanium alkoxides and condensates of hydrolyzates of titanium alkoxides; and
   (b) a β-keto ester compound expressed by general formula (1):

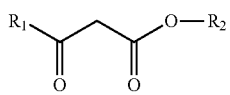
(1)

where $R_1$ and $R_2$ independently represent respective alkyl groups having 1 to 6 carbon atoms,
   wherein the β-keto ester compound is added at a mole content of 1.5 to 4.5 times of total moles of the sol-gel source material.

2. The barium titanate based coating liquid composition according to claim 1, wherein the sol-gel source material further contains (iii) at least a calcium component selected from the group consisting of calcium alkoxides, hydrolyzates of calcium alkoxides, and condensates of hydrolyzates of calcium alkoxides.

3. The barium titanate based coating liquid composition according to claim 1, wherein the sol-gel source material further contains (iv) at least a zirconium component selected from the group consisting of zirconium alkoxides, hydrolyzates of zirconium alkoxides, and condensates of hydrolyzates of zirconium alkoxides.

4. The barium titanate based coating liquid composition according to claim 1, further comprising:
   at least a metal alkoxide precursor selected from the group consisting of barium alkoxide precursors and titanium alkoxide precursors that can be formed by way of an interaction between the sol-gel source material and the β-keto ester compound.

5. The barium titanate based coating liquid composition according to claim 2, further comprising: a calcium alkoxide precursor formed by way of an interaction between the sol-gel source material and the β-keto ester compound.

6. The barium titanate based coating liquid composition according to claim 3, further comprising: a zirconium alkoxide precursor formed by way of an interaction between the sol-gel source material and the β-keto ester compound.

7. A method of manufacturing a barium titanate based coating liquid composition comprising:
   (1) a step of adding a β-keto ester compound to an organic solvent;
   (2) a step of adding, to the organic solvent, a sol-gel source material containing:
      (i) at least a barium component selected from the group consisting of barium alkoxides, hydrolyzates of barium alkoxides and condensates of hydrolyzates of barium alkoxides; and
      (ii) at least a titanium component selected from the group consisting of titanium alkoxides, hydrolyzates of titanium alkoxides and condensates of hydrolyzates of titanium alkoxides; and
   (3) a step of refluxing the organic solvent,
   wherein the β-keto ester compound is added at a mole content of 1.5 to 4.5 times of total moles of the sol-gel source material.

8. The method according to claim 7, wherein the step (2) includes adding the sol-gel source material further containing (iii) at least a calcium component selected from the group consisting of calcium alkoxides, hydrolyzates of calcium alkoxides, and condensates of hydrolyzates of calcium alkoxides.

9. The method according to claim 7, wherein the step (2) includes adding the sol-gel source material further containing (iv) at least a zirconium component selected from a group consisting of zirconium alkoxides, hydrolyzates of zirconium alkoxides and condensates of hydrolyzates of zirconium alkoxides.

10. A barium titanate based baked film, which is a baked film of the barium titanate based coating liquid composition according to claim 1, comprising:
    a perovskite type crystal expressed by general formula (2):

$$Ba_{1-x}Ca_xTi_{1-y}Zr_yO_3 (0 \leq x \leq 0.2, 0 \leq y \leq 0.2) \qquad (2)$$

and (111) oriented in pseudocubic notation.

11. An article comprising the barium titanate based baked film according to claim 10 formed on a metal electrode having the (111) orientation.

12. A liquid ejection head comprising:
    a liquid ejection orifice, a pressure chamber held in communication with the liquid ejection orifice, and an actuator for causing a capacity change of the pressure chamber to take place in order to eject liquid from the liquid ejection orifice,
    wherein the actuator comprises a vibrating plate, a lower electrode, a piezoelectric film, which is the barium titanate based baked film according to claim 10, and an upper electrode that are arranged in stated order as viewed from a side of the pressure chamber.

* * * * *